United States Patent [19]

Holzner

[11] Patent Number: 4,634,614
[45] Date of Patent: Jan. 6, 1987

[54] DEVICES FOR PERFUMING AMBIENT AIR AND ENCLOSED SPACES

[75] Inventor: Günter Holzner, Grand-Lancy, Switzerland

[73] Assignee: Firmenich S.A., Geneva, Switzerland

[21] Appl. No.: 653,267

[22] PCT Filed: Jan. 9, 1984

[86] PCT No.: PCT/CH84/00001
§ 371 Date: Sep. 13, 1984
§ 102(e) Date: Sep. 13, 1984

[87] PCT Pub. No.: WO84/02654
PCT Pub. Date: Jul. 19, 1984

[30] Foreign Application Priority Data
Jan. 14, 1983 [CH] Switzerland .................. 206/83

[51] Int. Cl.⁴ .................................................. A61L 9/04
[52] U.S. Cl. ....................................... 428/35; 428/76;
428/905; 206/484.1; 206/484.2; 239/55; 239/57
[58] Field of Search ............... 428/905, 35, 76; 239/55, 53, 57; 206/484, 484.1, 484.2

[56] References Cited

U.S. PATENT DOCUMENTS

| | | | |
|---|---|---|---|
| 1,831,677 | 11/1931 | March | 428/905 |
| 2,626,833 | 1/1953 | Valentine | 428/905 |
| 3,083,821 | 4/1963 | Woodson | 206/484 |
| 3,578,545 | 5/1971 | Carson et al. | 239/56 |
| 3,702,677 | 11/1972 | Heffington | 239/55 |
| 4,130,245 | 12/1978 | Bryson | 239/56 |
| 4,145,001 | 3/1979 | Weyenberg et al. | 239/56 |
| 4,157,787 | 6/1979 | Schwartz | 239/56 |
| 4,161,283 | 7/1979 | Hyman | 239/55 |
| 4,285,468 | 8/1981 | Hyman | 239/55 |

FOREIGN PATENT DOCUMENTS 1516845 7/1978 United Kingdom .

*Primary Examiner*—John E. Kittle
*Attorney, Agent, or Firm*—Pennie & Edmonds

[57] ABSTRACT

A device for perfuming ambient air or closed locals comprises a chamber having at least one polymer wall allowing the diffusion of active odoriferous substance vapors into the environning medium, the polymer wall being covered with a thin layer of paper coated with a polymer sheet to which adheres a protection sheet which is impervious to the active substance vapors. Such a device has the advantage of providing for the preservation of the active substance without any loss during prolonged periods of time before use.

5 Claims, 6 Drawing Figures

DEVICES FOR PERFUMING AMBIENT AIR AND ENCLOSED SPACES

The international application WO No. 81/00051 published on Jan. 22, 1981 discloses an object which is impervious to liquids and is intended for perfuming ambient air or enclosed spaces, characterized in that it contains a perfuming composition enriched with substances which may or may not be fragrant and have low polarity and in that the object has at least one polymeric wall enabling active fragrant ingredients to be diffused towards the exterior.

The French patent application FR A No. 20 91 855, published on Jan. 21, 1972, relates to a device for the continuous diffusion of purifying agent vapours, which device comprises a permeation wall made of macromolecular material, one face of which is in contact with the volatile purifying agent which impregnates a fibrous mass covered by the permeation wall.

The French patent application FR A No. 23 36 946, published on July 29, 1977, relates to a slow diffusion air-freshening system which comprises a chamber and a perfume contained in the said chamber, at least one surface of the said chamber being a polymer film. Likewise in this system the perfume is impregnated in a support such as silica, talc, glass wool or blotting paper.

The U.S. Pat. No. 3,578,545, published on May 11, 1971, relates to a flexible laminated substance releasing a perfume and comprising a fabric support impregnated with a perfume, surrounded by a porous plastic film and permeable to perfume vapours.

The U.S. Pat. No. 4,161,283, published on July 17, 1979, describes a device for continuously diffusing purifying vapours; the said device comprises an outer wall formed by a polymeric material enabling molecular diffusion and an impermeable inner wall. The outer wall is in addition covered with an impermeable sheet suitable for preventing the diffusion of the active volatile substances during storage.

A similar device is described in the U.S. Pat. No. 4,285, 468, published on Aug. 25, 1981.

As the purifying articles described in the prior art are all constituted by a system comprising a polymeric diffusion wall, they should have a device for preventing the active perfuming elements from diffusing into the environment during storage.

To this end, the international application WO No. 81/00051 describes a method consisting in applying a Surlyn ® type polymeric sheet (origin: Du Pont de Nemours) on the walls, through which diffusion normally occurs. This type of polymeric sheet may adhere by hot welding to polyethylene or polypropylene and be detached just before use. For the same purpose, a further method consists in using aluminium sheets welded to polypropylene foam.

A problem arises, however, during extended storage of such devices before they are sold; owing to the diffusion of the perfume vapours through the polymeric walls of the packing, an appreciable loss of the initial amount of the active substance has been observed. In order to overcome this disadvantage, a multi-chamber device has recently been developed (cf. international patent application WO No. 82/02700 published on Aug. 19, 1982). In a device of this type, the active perfuming substance is kept in a compartment having walls which are impermeable to perfume vapours and one join of which may be broken under the effect of external pressure and subsequently, just before use, when the walls of the said join have been broken, the solution passes into a compartment having walls made of polymeric material permeable with respect to the perfume vapours which can then diffuse uniformly into the ambient atmosphere.

A device of this type is highly efficient in use, however the manufacture thereof requires an improved apparatus to be produced and a rigorous assembly procedure.

In order to remedy such disadvantages the present invention proposes a novel solution based on a simple procedure.

The principle on which the invention is based consists in the direct assembly by welding of a thin layer of paper on the external wall of the polymeric membrane through which the diffusion of the active substance vapours occurs. This thin paper layer is then covered with a polymeric material sheet, for example of the Surlyn ® type having a polyethylene base, on which a metal sheet, preferably an aluminium sheet, for example, is finally welded. A metal sheet of this type constitutes an impermeable barrier with respect to the active substance vapours by preventing their molecular diffusion towards the exterior. Of course, other materials may also be suitable for this purpose, provided that they have an adequate coefficient of impermeability.

The present invention therefore relates to a device for perfuming ambient air or enclosed spaces, which device comprises a chamber having at least one polymeric material wall enabling the vapours of the active fragrant substance to diffuse into the environment, characterized in that the external surface of the said polymeric wall is covered with a thin layer of paper, the said layer being covered by a sheet of polymeric material to which a metal sheet adheres.

By using the device according to the invention, the active solution may be kept without any losses for extended periods of time before being used. At the desired moment, the user could, on the other hand, easily tear the packing partially or completely and thus enable the active substance to diffuse towards the exterior of the chamber.

The attached drawings are given by way of non-limiting example.

For other embodiments reference may be made to the particular devices disclosed in the prior art. The principle advantage provided by the device according to the invention resides not only in the simplicity of its assembly but also in the fact that the tear is effected in a particularly accurate manner along a longitudinal axis. Since the paper layer may adhere directly to the permeable polymeric wall by welding, without an adhesive having to be used, the diffusion of the vapours of the active substance is not hampered at all. In addition, it cannot be denied that from the aesthetic point of view the solution according to the present invention offers many advantages: the tear in the paper layer leaves the device with a homogeneous surface.

Using paper as an element of the protective layer has already been proposed in the prior art. Its use, however, was restricted either to containing directly the active substance (according to the U.S. Pat. No. 3,702,677) or to protecting an adhesive layer placed on the impermeable wall so as to enable the device to adhere to a vertical or inclined surface (according to the U.S. Pat. No. 4,161,283, column 4, line 30 ff.).

As indicated with respect to the devices of the prior art, the impermeable walls may be constituted by sheets of polyamide, polyester, polyethylene, polypropylene or any other polymeric material generally used for the manufacture of packing sheets.

The permeable wall is, however, to be constituted by the same materials described in the prior art (cf. in this respect the international application No. 81/00051).

As regards the nature of the paper forming the layer which can be torn, it may consist of natural or artificial fibres or mixtures of the two. These products are commercially available and 47251/1 or 46674 of the Balsthal firm (Balsthal, Switzerland) may be cited by way of example. A crêpe type of tissue paper is thoroughly suitable. The thickness of the paper layer obviously affects the speed of diffusion of the active vapours. However, this factor is not decisive. We have been able to observe that figures between approximately 20 and 100 were perfectly satisfactory. The weight of the paper per unit area may be between 20 and 100 gr/m$^2$.

Evidently, both the device according to the invention and the chamber of this device containing the active substance may be manufactured in a wide variety of shapes so as to satisfy functional and aesthetic criteria. For this purpose, the person skilled in the art may devise solutions appropriate to the particular uses which he will be asked to study.

The device according to the invention may, for example, be used in a casing in which this same device could slide depending on the portion of the surface of the permeable wall which is required to be used, so as to regulate the speed of diffusion.

Figure 1:
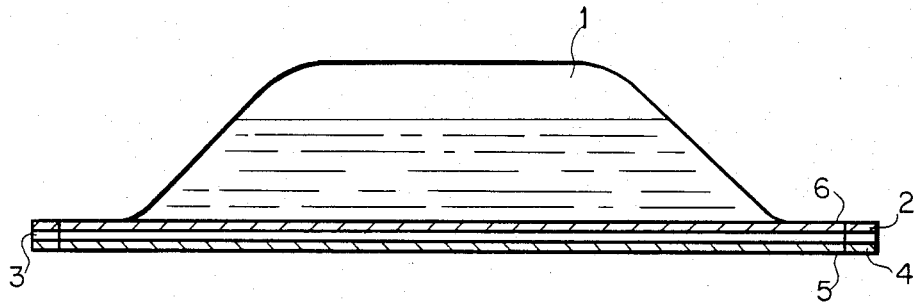
FIG. 1 shows a transverse section of a filled device, provided according to a particular embodiment of the invention. It consists in particular of a chamber (1) containing the active substance, a permeable polymeric wall (2), a thin paper layer (3), a polymeric sheet (4) and an outer metal sheet (5). (6) defines a welding or indentation zone.
Figure 2:
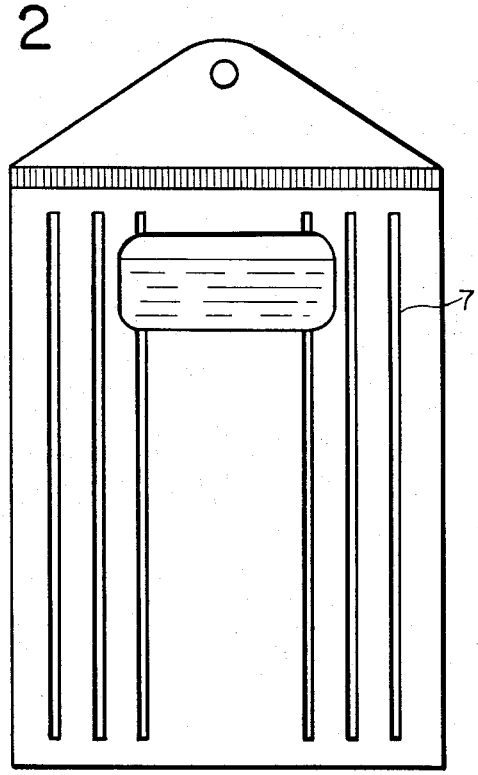
FIG. 2 shows a particular embodiment of the device according to the invention. This embodiment comprises a plurality of grooves (7) in the permeable wall or walls, which form the "cannulae" through which the active substance can infiltrate. The diffusion thereof is therefore improved.
Figure 3:
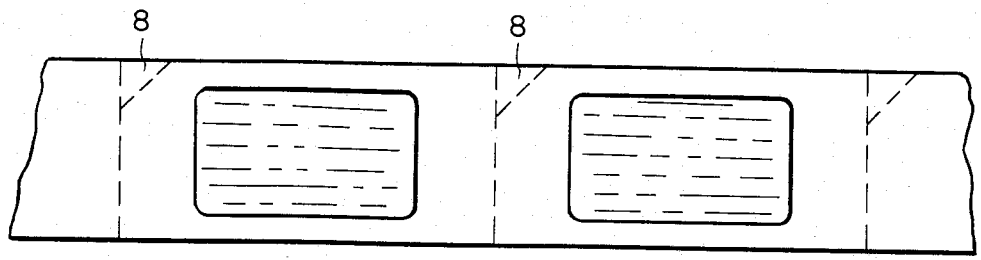
FIG. 3 shows the devices arranged in a row. The user may tear the protective layers, successively exposing each of the permeable polymeric walls. In order to facilitate tearing, a tab (8) may be provided in one corner of the device.
Figure 4:
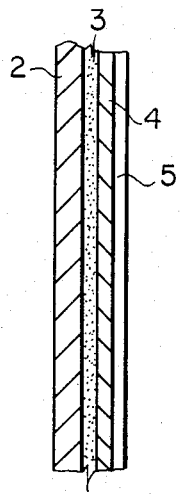
FIG. 4 is an enlarged section of the permeable wall covered with the protective layer: paper (3), polymeric sheet (4) and metal sheet (5).
Figure 5:
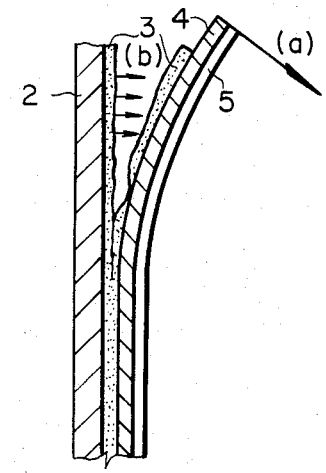
FIG. 5 shows this same part when stress (a) is applied on the outer protective layer. In this way the paper layer tears along the longitudinal axis and, under the effect of the stress (b), the vapours of the active substance diffuse through the wall (2) and the residual paper (3).
Figure 6:
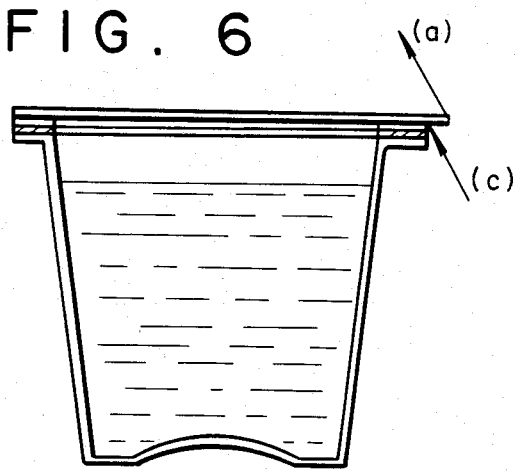

The principle on which the present invention is based may be used in ways other than that described above in the field of ambient air purifiers. Such a principle may be extended to the production of hermetic closures for all types of containers which need to be opened after a storage period. By way of example there may be cited receptacles containing foodstuffs such as yogourts or custards. Containers of this type, generally made of plastics material, are principally closed by means of a lid consisting of a metal sheet. Under the effect of the welding it is often difficult to open the lid and it may even tear under the stress exerted during opening. A disadvantage of this type can be eliminated in a device having a lid fixed by welding to a container, whose contact join with the said lid comprises a thin layer of paper to which the lid adheres. FIG. 6 shows an example of the use of such a device. When a stress (a) is exerted in order to open it, there is a uniform transverse tear along the paper layer (c).

I claim:

1. A device for perfuming ambient air or enclosed spaces which comprises at least one chamber containing an active fragrant substance and having at least one wall made of polymeric material enabling the vapours of the active fragrant substance to diffuse into the environment, the outer surface of said polymeric wall being covered with a thin paper layer, said layer being covered with a sheet of polymeric material to which there adheres a sheet of protective material impermeable to the vapours of the active substance.

2. A device as claimed in claim 1 wherein the protective material is aluminium.

3. A device as claimed in claim 1, containing a plurality of chambers.

4. A device for perfuming ambient air or enclosed spaces which comprises at least one chamber containing an active fragrant substance and having at least one wall made of polymeric material enabling the vapours of the active fragrant substance to diffuse into the environment, the outer surface of said polymeric wall being covered with a thin paper layer, said layer being covered with a sheet of polymeric material to which there adheres a sheet of protective material impermeable to the vapours of the active substance, and having grooves in the polymeric wall, thereby increasing the surface area of said wall exposed to the vapours of the active fragrant substance.

5. A device for perfuming ambient air or enclosed spaces which comprises a plurality of chambers containing an active fragrant substance and having walls made of polymeric material enabling the vapours of the active fragrant substance to diffuse into the environment, the outer surfaces of said polymeric walls being covered with thin paper layers, said layers being covered with sheets of protective material impermeable to the vapours of the active substance, and having grooves in the polymeric walls, thereby increasing the surface areas of said walls exposed to the vapours of the active fragrant substance.

* * * * *